US011730615B2

(12) United States Patent
Wang et al.

(10) Patent No.: US 11,730,615 B2
(45) Date of Patent: Aug. 22, 2023

(54) VASCULAR STENT (71) Applicant: Shenzhen Lifetech Endovascular Medical Co., Ltd., Shenzhen (CN)

(72) Inventors: Yifei Wang, Shenzhen (CN); Benhao Xiao, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 132 days.

(21) Appl. No.: 17/418,648

(22) PCT Filed: Oct. 9, 2019

(86) PCT No.: PCT/CN2019/110124
§ 371 (c)(1),
(2) Date: Jun. 25, 2021

(87) PCT Pub. No.: WO2020/134317
PCT Pub. Date: Jul. 2, 2020

(65) Prior Publication Data
US 2022/0079783 A1 Mar. 17, 2022

(30) Foreign Application Priority Data

Dec. 28, 2018 (CN) .......................... 201811625677.9

(51) Int. Cl.
*A61F 2/848* (2013.01)
*A61F 2/844* (2013.01)
(Continued)

(52) U.S. Cl.
CPC .............. *A61F 2/848* (2013.01); *A61F 2/844* (2013.01); *A61F 2/852* (2013.01);
(Continued)

(58) Field of Classification Search
CPC .... A61F 2/844; A61F 2/848; A61F 2002/821; A61F 2/82
See application file for complete search history.

(56) References Cited

U.S. PATENT DOCUMENTS 9,125,738 B2    9/2015   Figulla et al.
10,076,410 B2   9/2018   Quijano et al.
(Continued)

FOREIGN PATENT DOCUMENTS

CN      102470031 A     5/2012
CN      102470031 A     5/2012
(Continued)

OTHER PUBLICATIONS

Office Action dated Jul. 6, 2022 for corresponding India Application No. 202127033636.
(Continued)

*Primary Examiner* — William H Matthews
(74) *Attorney, Agent, or Firm* — Raymond Sun (57) ABSTRACT A vascular stent, including an inner stent tube as well as a proximal support and a distal support which are arranged on an outer wall of the inner stent tube. When the vascular stent is in a compressed configuration, the proximal support and the distal support are both folded and close to the outer wall of the inner stent tube; when the vascular stent is expanded from the compressed configuration to an expanded configuration, a free end of the proximal support expands towards the distal end of the vascular stent, and a free end of the distal support expands towards the proximal end of the vascular stent. The vascular stent can be anchored to a main stent tube in a blood vessel by the proximal support and the distal support, preventing the vascular stent from shifting or becoming dislodged after being transplanted into the main stent tube.

9 Claims, 6 Drawing Sheets (51) Int. Cl.
*A61F 2/852* (2013.01)
*A61F 2/82* (2013.01)

(52) U.S. Cl.
CPC ... *A61F 2002/821* (2013.01); *A61F 2002/828* (2013.01); *A61F 2210/0076* (2013.01); *A61F 2220/0025* (2013.01)

(56) References Cited

U.S. PATENT DOCUMENTS

| | | |
|---|---|---|
| 10,695,164 B2 | 6/2020 | Li |
| 2001/0016766 A1 | 8/2001 | Vardi et al. |
| 2003/0236567 A1 | 12/2003 | Elliot |
| 2004/0093078 A1 | 5/2004 | Moll et al. |
| 2012/0179236 A1 | 7/2012 | Benary et al. |
| 2014/0046347 A1 | 2/2014 | Cully et al. |
| 2019/0175327 A1 | 6/2019 | Xiao et al. |

FOREIGN PATENT DOCUMENTS

| | | |
|---|---|---|
| CN | 103476362 A | 12/2013 |
| CN | 103932826 A | 7/2014 |
| CN | 103932826 A | 7/2014 |
| CN | 105473105 A | 4/2016 |
| CN | 105473105 A | 4/2016 |
| CN | 107822739 A | 3/2018 |
| CN | 107822739 A | 3/2018 |
| CN | 108261250 A | 7/2018 |
| CN | 108309374 A | 7/2018 |
| CN | 109700567 A | 5/2019 |
| CN | 109700567 A | 5/2019 |
| GB | 2515731 A | 1/2015 |
| WO | WO2013/026584 A1 | 2/2013 |

OTHER PUBLICATIONS

European Search Report dated Aug. 25, 2022 for corresponding Application No. EP 19 90 3169.
First Office Action for corresponding China Application No. 201811625677.9.
Translation of First Office Action for corresponding China Application No. 201811625677.9.
Response (and amended claims) to Office Action for corresponding China Application No. 201811625677.9.
Translation of Response (and amended claims) to Office Action for corresponding China Application No. 201811625677.9.
Notification of Grant for corresponding China Application No. 201811625677.9.
Translation of Notification of Grant for corresponding China Application No. 201811625677.9.
International Search Report dated Jun. 1, 2020 for corresponding PCT Application No. PCT/CN2019/110124.
CN 109700567 A (Dongguan Xianjian Changtong Medical Co., Ltd.) May 3, 2019 (May 3, 2019) claims 1-10.
CN 102470031 A (Endospan Ltd.) May 23, 2012 (May 23, 2012) description, paragraphs [0098]-[0116] and [0121], and figures 2, 3 and 4D.
CN 105473105 A (Navigate Cardiac Structures, Inc.) Apr. 6, 2016 (Apr. 6, 2016) description, paragraphs [0068]-[0077], and figures 4-8.
CN 107822739 A (Lifetech Scientific (Shenzhen) Co., Ltd.) Mar. 23, 2018 (Mar. 23, 2018) description, paragraph [0065], and figure 12B.
GB 2515 731 A (Vascutek Limited) Jan. 7, 2015 (Jan. 7, 2015) entire document.
US 2001016766 A1 (Vardi, G.M. et al.) Aug. 23, 2001 (Aug. 23, 2001) entire document.
CN 103932826 A (M.I.Tech Co., Ltd.) Jul. 23, 2014 (Jul. 23, 2014) entire document.

VASCULAR STENT

FIELD

The disclosure relates to the technical field of interventional medical devices, in particular to a vascular stent.

BACKGROUND

This section provides background information related to the present disclosure only and is not necessarily prior art.

In the prior art, when endovascular repair is used for treating an aortic dissection or an aortic aneurysm, it is often difficult to implant a large stent into a blood vessel due to an insufficient length of an anchoring area at a proximal end of the large stent, and at this time, some experienced doctors choose to increase the anchoring area at the proximal end of the large stent by means of establishing an anchoring area covering the branch vessel, where Chimney techniques or in-situ fenestration techniques are the most commonly used techniques for establishing an anchoring area covering a branch vessel.

Figure 1:
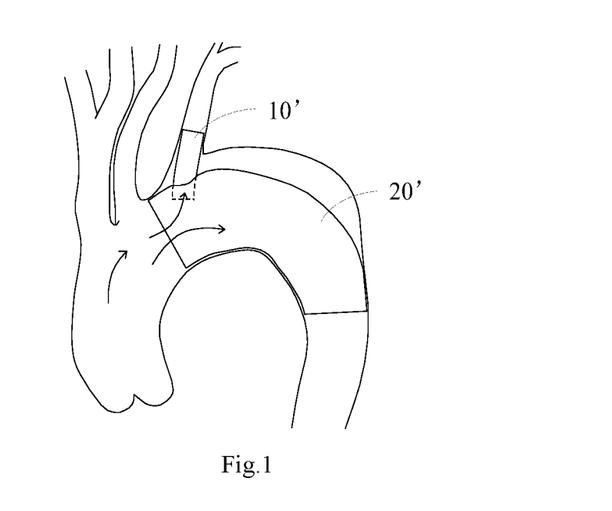
FIG. 1 is a structural schematic view showing a branch stent tube in the prior art being implanted into a fenestration site of a main stent tube.
Figure 2:
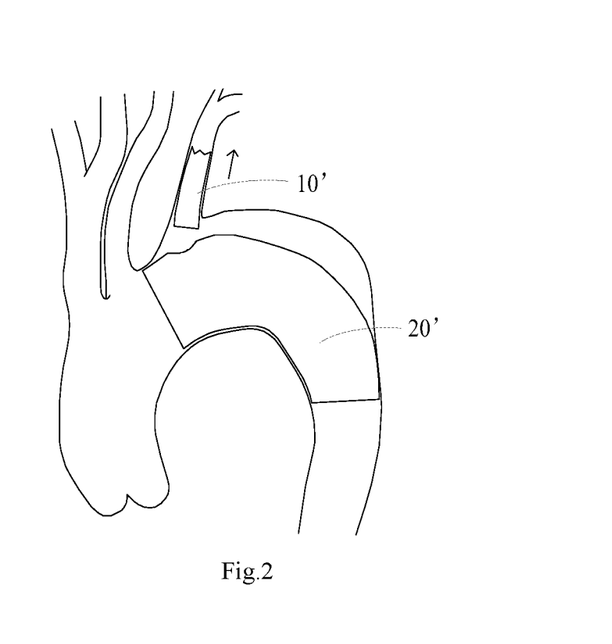
FIG. 2 is a structural schematic view showing the branch stent tube of FIG. 1 becoming dislodged from the fenestration site of the main stent tube and falling into a branch vessel.
Figure 3:
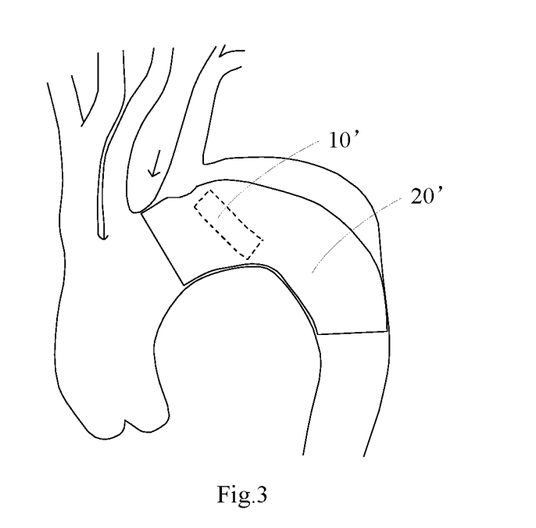
FIG. 3 is a structural schematic view showing the branch stent tube of FIG. 1 falling off from the fenestration site of the main stent tube and falling into the main stent tube.

As shown in FIG. 1, the branch vessel opened by the in-situ fenestration techniques tends to form thrombus due to the shape of the fenestra in a main stent tube 20' and the swinging of a film at the fenestration site after the fenestration under the flushing of blood, and even the phenomenon of re-blocking the blood flow in the branch vessel can occur. Therefore, after the main stent tube 20' is fenestrated in situ, a branch stent tube 10' is generally implanted into the fenestration site of the main stent tube 20' to fix the fenestration site and ensure the normal blood supply of the branch vessel. However, as shown in FIGS. 2 and 3, the mechanical properties of the branch stent tube 10' itself may also present some safety hazards: as an aortic arch pulsates, the branch stent tube 10' tends to move, and even when an anchoring force of the branch stent tube 10' is weak, the branch stent tube 10' may become dislodged and fall into a distal end of the branch vessel or into an aorta (the direction indicated by an arrow in FIGS. 2 and 3 is the direction in which the branch stent tube 10' falls off).

Therefore, it is necessary to provide a new vascular stent in order to solve the technical problem that the existing branch stent tube 10' can easily shift or become dislodged after being implanted into the fenestration site of the main stent tube 20'.

SUMMARY OF THE INVENTION

Based on the above problems existing in the vascular stent in the prior art, the disclosure provides a novel vascular stent which can effectively reduce the possibility of shifting or falling off of the vascular stent after it is implanted into a main stent tube, which is implemented by the following technical scheme.

The disclosure provides a vascular stent including an inner stent tube as well as a proximal support and a distal support which are arranged on an outer wall of the inner stent tube. When the vascular stent is in a compressed configuration, the proximal support and the distal support are both folded and close to the outer wall of the inner stent tube; and when the vascular stent is expanded from the compressed configuration to an expanded configuration, a free end of the proximal support expands towards a distal end of the vascular stent, and a free end of the distal support expands towards a proximal end of the vascular stent.

In one embodiment, the proximal support includes a plurality of first supports disposed along a circumferential direction of the inner stent tube, connecting ends of the plurality of first supports are each connected to the outer wall of the inner stent tube, and free ends of the plurality of first supports are each directed towards an outside of the inner stent tube.

In one embodiment, a minimum included angle between a straight line or plane in which the first support is located and a central axis of the vascular stent ranges from 20° to 80° in the expanded configuration or a natural configuration.

In one embodiment, the proximal support is provided with at least a layer of film.

In one embodiment, the distal support includes a plurality of second supports disposed along a circumferential direction of the inner stent tube, connecting ends of the plurality of second supports are each connected to the outer wall of the inner stent tube, and free ends of the plurality of second supports are each directed towards a proximal end of the inner stent tube.

In one embodiment, a minimum included angle between a straight line or plane in which the second support is located and the central axis of the vascular stent ranges from 5° to 30° in the expanded configuration or the natural configuration.

In one embodiment, in the expanded configuration, the free end of the proximal support is closer to the distal end of the vascular stent than the free end of the distal support.

In one embodiment, the free end of the distal support is connected to the connecting end of the proximal support by means of a flexible connector, and the free end of the proximal support expands towards the distal end of the vascular stent during expansion.

In one embodiment, the flexible connector is the coating film, both ends of which cover on the proximal support and the distal support, respectively.

In one embodiment, a length of the flexible connector is greater than 0 mm and less than or equal to 2 mm.

It will be appreciated by those skilled in the art that in the technical scheme of the disclosure, the vascular stent is provided with a proximal support and a distal support on the outer wall of the inner stent tube, and when the vascular stent is in a compressed configuration, the proximal support and the distal support are both folded over and positioned close to the outer wall of the inner stent tube; when the vascular stent is implanted into the main stent tube, the vascular stent is in an expanded configuration, at which time the free end of the proximal support expands towards the distal end of the vascular stent, and the free end of the distal support expands towards the proximal end of the vascular stent, so that the proximal support and the distal support on the vascular stent respectively expand and then are respectively anchored to the main stent tube, and the vascular stent is fixed on the main stent tube, thereby preventing the vascular stent from shifting or becoming dislodged from the main stent tube.

BRIEF DESCRIPTION OF THE DRAWINGS

Various other advantages and benefits will become apparent to those of ordinary skill in the art upon reading the following detailed description of the preferred implementations. The drawings are only for purposes of illustrating the preferred implementations and are not to be construed as limiting the disclosure. Also throughout the drawings, like reference numerals designate like components. In the drawings.

Where, 10', branch stent tube; 20' main stent tube; 10, first vascular stent; 11, first inner stent tube; 111, first inner stent tube framework; 112, the first inner stent tube film covering; 12, first proximal support; 121, first supporting rod; 121a, first connecting end; 121b, first free end; 122, first proximal support film covering; 13, first distal support; 131, second supporting rod; 131a, second connecting end; 131b, second free end; 20, second vascular stent; 21, second inner stent tube; 22, second proximal support; 23, second distal support; 30, third vascular stent; 31, third inner stent tube; 32, third proximal support; 33, third distal support; 34, flexible connector; A, aorta tube; B, branch vessel; C, main stent tube; L, central axis; M, perpendicular to the central axis L.

DETAILED DESCRIPTION OF THE DISCLOSURE

Exemplary implementations of the disclosure will be described in more detail below with reference to the accompanying drawings. Although exemplary implementations of the disclosure are shown in the drawings, it should be understood that the disclosure may be embodied in various forms and should not be limited to the implementations set forth herein. Rather, these implementations are provided so that this disclosure will be thoroughly understood, and the scope of the disclosure will be fully conveyed to those skilled in the art. It should be noted that the disclosure is described by providing a proximal support and a distal support as a rod-like structure and a connecting rod structure, but is not limited to the shape structure of the proximal support and the distal support of the disclosure. For example, the proximal support and the distal support of the disclosure may have other structures such as a folded plate-like structure, and such adjustment is within the scope of the disclosure for proximal and distal supports.

It is to be understood that the terminology used herein is for the purpose of describing particular example implementations only and is not intended to be limiting. As used herein, the singular forms "a/an", "one" and "the" are intended to include the plural forms as well, unless the context clearly indicates otherwise. The terms "comprising", "including", "containing", and "having" are inclusive and thus specify the presence of stated features, steps, operations, elements, and/or components, but do not preclude the presence or addition of one or more other features, steps, operations, elements, components, and/or groups thereof. The method steps, processes, and operations described herein are not to be construed as necessarily requiring them to be executed in the particular order described or illustrated, unless the order of execution is explicitly indicated. It should also be understood that additional or alternative steps may be used.

While the terms first, second, third, etc. may be used herein to describe various elements, components, regions, layers and/or sections, these elements, components, regions, layers and/or sections should not be limited by these terms. These terms may be used solely to distinguish one element, component, region, layer or section from another region, layer or section. Terms such as "first", "second" and other numerical terms used herein do not imply a sequence or order unless the context clearly dictates otherwise. Accordingly, a first element, component, region, layer or section discussed below may be referred to as a second element, component, region, layer or section without departing from the teachings of example implementations.

For ease of description, spatially relative terms, such as "inner", "inner wall", "outer wall", "close to", "proximate", "away from", "inner side", "outer side", "below", "under", "above", "over", etc. may be used herein to describe the relationship of one element or feature to another element or feature as shown in the figures. Such spatially relative terms are intended to encompass different orientations of the apparatus in use or operation in addition to the orientation depicted in the figures. For example, if the apparatus in the figures flips or reverses, elements described as "below" or "under" other elements or features would then be oriented "above" or "over" the other elements or features. Thus, the example term "under" may include both an upper and a lower orientation. The apparatus may be otherwise oriented (rotated 90 degrees or in other directions) and the spatially relative descriptors used herein interpret accordingly.

It should be noted that in the field of stents, it is common to refer to an end of the stent where blood flow enters the blood vessel as a "proximal" end of the stent (the direction of an arrow shown in FIG. 1 is the direction where blood flow enters the blood vessel) and an end of the stent where blood flow exits the blood vessel as a "distal" end of the stent, and the "proximal" and "distal" ends of any component of the stent are defined in accordance with this principle. "Axial" generally refers to the lengthwise direction of the stent as it is delivered, and "radial" generally refers to the direction of the stent perpendicular to its "axial" direction, and the "axial" and "radial" directions of any component of the covered stent are defined in accordance with this principle. "Compressed configuration" refers to a configuration in which a medical device, such as a stent, is accommodated in an assembly, such as a sheath, and thus compressed during delivery; "expanded configuration" refers to a configuration in which a medical device in a compressed configuration expands in a self-expansion manner after being free from the constraint of an assembly, such as a sheath. When a device can expand in a self-expansion manner in a natural state, and is only acted upon by gravity, the configuration corresponds to a "natural configuration".

In order to describe the technical features and technical effects of the vascular stent of the disclosure in detail, the vascular stent of the disclosure is described below by three specific embodiments.

Embodiment 1

Figure 4:
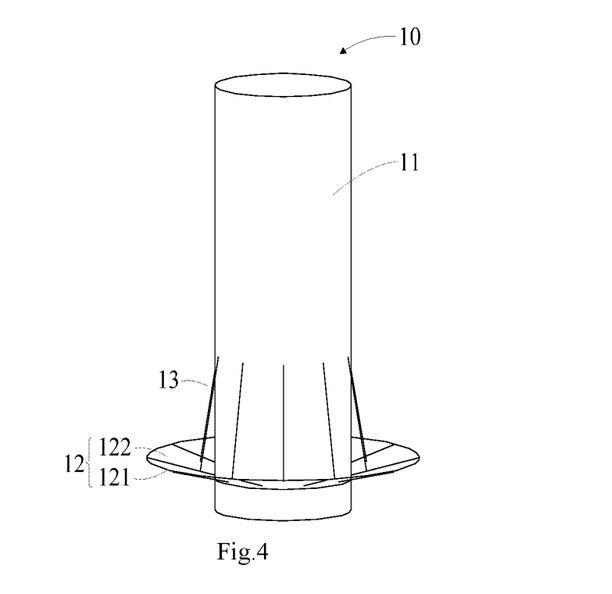
FIG. 4 is a structural schematic view of a first vascular stent according to a first embodiment of the disclosure.
Figure 5:
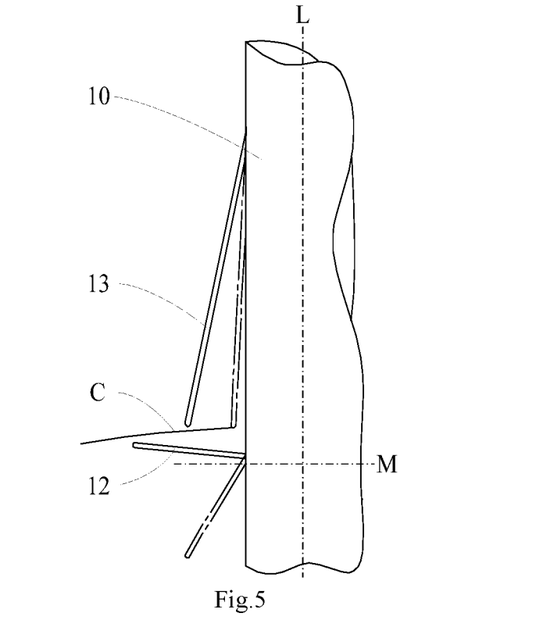
FIG. 5 is a structural schematic view of flipping trajectories of a proximal support and a distal support on the first vascular stent shown in FIG. 4.

As shown in FIG. 4, the present embodiment provides a first vascular stent 10 including a first inner stent tube 11, a first proximal support 12, and a first distal support 13, the first proximal support 12 and the first distal support 13 are respectively arranged on outer walls of the first inner stent tube 11. As shown in FIG. 5, when the first vascular stent 10 is in the compressed configuration, the first proximal support 12 and the second distal support 13 are both in a folded state and positioned close to the outer wall of the first inner stent tube 11 (shown in dotted lines in FIG. 5); when the first vascular stent 10 is transformed from the compressed configuration to the expanded configuration, the first proximal support 12 expands towards the direction of a distal end of the first vascular stent 10, and the second distal support 13 expands towards a proximal end of the first vascular stent 10.

Figure 6:
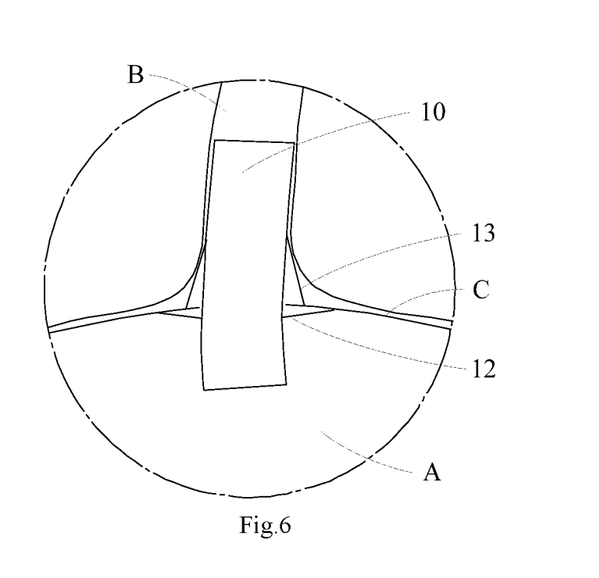
FIG. 6 is a structural schematic view showing the first vascular stent shown in FIG. 4 being implanted into the main stent tube.

Specifically, as shown in FIG. 6, the first vascular stent 10 in this embodiment is adapted to be implanted into a branch vessel B and anchored to a main stent tube C in an aorta tube A, a fenestra (not shown) is formed in the wall of the main stent tube C at a position corresponding to the branch vessel B, and after the first vascular stent 10 is released in vivo, since the first proximal support 12 expands towards the distal end of the first vascular stent 10 and finally abuts against the inner wall of the main stent tube C, the first distal support 13 expands away from the outer wall of the first inner stent tube 11; that is, the first distal support 13 expands towards the proximal end of the first vascular stent 10 and finally abuts against the outer wall of the main stent tube C, so that the first vascular stent 10 can be anchored at a fenestration site of the main stent tube C by means of the first proximal support 12 and the first distal support 13, thereby preventing the first vascular stent 10 from shifting or dislodging, and making the main stent tube C more stable after being implanted into the body and preventing shifting.

Figure 7:
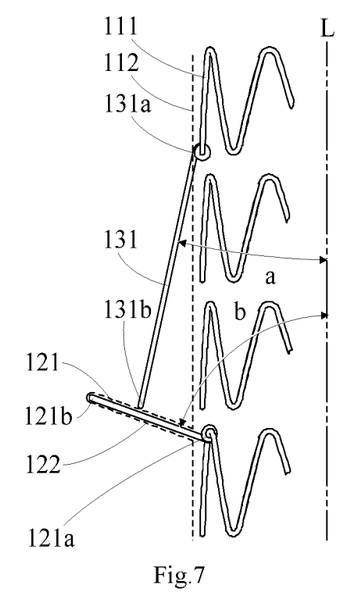
FIG. 7 is a schematic view of a portion of an internal structure of the first vascular stent shown in FIG. 4.

As shown in FIG. 7, a first connecting end 121a of the first proximal support 12 is rotatably connected to a first inner stent tube framework 111 and the first free ends 121b of the first proximal support 12 are all directed towards the outside of the first inner stent tube 11 and can automatically extend and abut against the inner wall side of the main stent tube C near the fenestration site after being released. The first distal support 13 is arranged on the outer wall of the first vascular stent 10 and located at the outer wall side near the fenestration site of the main stent tube C, a second connecting end 131a of the first distal support 13 is rotatably connected to the first inner stent tube framework 111 and the second free ends 131b of the first distal support 13 are all directed towards the proximal end of the first inner stent tube 11, and can automatically extend and abut against the outer wall side near the fenestration site of the main stent tube C after being released. In other embodiments, the first connecting end 121a of the first proximal support 12 is fixedly connected to the first inner stent tube framework 111 but can automatically expand to a pre-set shape after being freed from the radial constraint of the sheath, at which time the first free end 121b of the first proximal support 12 abuts against the inner wall of the main stent tube C; similarly, the second connecting end 131a of the first distal support 13 is fixedly connected to the first inner stent tube framework 111 but can automatically expand to a pre-set shape after being freed from the radial constraint of the sheath, at which time the second free end 131b of the first distal support 13 abuts against the outer wall of the main stent tube C.

The nickel-titanium wires are knitted and subjected to heat-setting treatment to form a metal wave ring consisting of a plurality of wave crests, a plurality of wave troughs and a plurality of side rods, and a plurality of metal wave rings are arranged along the central axis L to form the first inner stent tube framework 111. A first inner stent tube film covering 112 is formed by sintering ePTFE, and the first inner stent tube film covering 112 is coated on the inner and outer surfaces of the first inner stent tube framework 111 to thereby form the first inner stent tube 11. The metal wave ring can also be made of metal or polymer materials with shape memory by laser cutting.

Referring to FIG. 4 again, the first proximal support 12 consists of a plurality of first supporting rods 121 and a first proximal support film covering 122, the plurality of first supporting rods 121 are a plurality of rods made of metal (e.g. Nitinol) with shape memory characteristic, the plurality of first supporting rods 121 circumferentially surround the outer wall of the first inner stent tube 11 and are spaced apart from one another. The first connecting ends 121a of the plurality of first supporting rods 121 are connected to the first inner stent tube framework 111 in a winding manner, and are heat-treated and shaped to form a preset included angle of 80° with the central axis L of the first inner stent tube 11, and can naturally rebound to the preset angle after being released from the compressed configuration; the preset included angle ranges from 20° to 80°, and the larger the preset included angle is, the larger the surface area of the first proximal support 12 would be, and blood flow can be better prevented from flowing through the gap between the main stent tube C and the first inner stent tube 11, so that internal leakage is prevented. The first proximal support film covering 122 is coated on the plurality of first supporting rods 121 by means of heat treatment or sewing, and is hermetically connected to the first inner stent tube film covering 112 on the first inner stent tube 11 at the first connecting ends 121a of the first supporting rods 121; the first proximal support film covering 122 may be one or more layers.

The first distal support 13 consists of a plurality of second supporting rods 131 circumferentially surrounding the outer wall of the first inner stent tube 11, and the plurality of second supporting rods 131 are spaced apart and are not connected to one another. The second connecting end 131a of the second supporting rod 131 is connected to the first inner stent tube framework 111 in a winding manner. The second supporting rod 131 is made of a metal material with shape memory characteristic (e.g. Nitinol material) being knitted or cut, and the second supporting rod 131 is heat-treated and shaped to form a preset included angle of 15° with the central axis L of the first inner stent tube 11, and can naturally rebound to the preset angle after being released from the compressed configuration.

Referring to FIGS. 5 and 6 together, when one end of the first vascular stent 10 passes through the fenestra of the main stent tube C, the first proximal support 12 of the first vascular stent 10 is located inside the main stent tube C in the aortic tube A, and the first distal support 13 of the first vascular stent 10 is located outside the main stent tube C in the branch vessel B. When the first vascular stent 10 is released in vivo, the motion trajectory of the first proximal support 12 is a large-angle flip (perpendicular M across the central axis L of the first vascular stent 10) from the proximal end of the first vascular stent 10 to the distal end of the first vascular stent 10; until the first free end 121b of the first proximal support 12 abuts against the inner wall of the main stent tube C, the motion trajectory of the first distal support 13 is that its second free end 131b drives the first distal support 13 to expand at a small angle in a direction away from the outer wall of the first vascular stent 10; until the second free end 131b of the first distal support 13 abuts against the outer wall of the main stent tube C, so that the first vascular stent 10 is anchored to the main stent tube C, avoiding shifting of the first vascular stent 10 relative to the main stent tube C.

When the first vascular stent 10 is in the compressed configuration, the first proximal support 12 and the first distal support 13 on the first vascular stent 10 are both folded and positioned close to the outer wall of the first vascular stent 10, so that the first vascular stent 10 can be smoothly delivered in the body after being accommodated in a sheath of a delivery device. After the first vascular stent 10 is delivered to the target area in the blood vessel by the delivery device to be released, the first proximal support 12 and the first distal support 13 on the first vascular stent 10 are restored to their respective expanded states due to the shape memory, so that the first vascular stent 10 is anchored to the main stent tube C in the blood vessel, and the first vascular stent 10 is unlikely to experience shifting or become dislodged.

In another embodiment, the lengths of the plurality of second supporting rods 131 on the first distal support 13 may be the same or different, and the plurality of second free ends 131b of the plurality of second supporting rods 131 may still abut against the outer wall of the main stent tube C when the angle of inclination of the branch vessel B with respect to the aorta vessel A is large.

The plurality of first supporting rods 121 of the first proximal support 12 and the plurality of second supporting rods 131 of the first distal support 13 may be distributed in one-to-one correspondence along the circumferential direction of the first vascular stent 10, respectively, and may be staggered. The total number of first supporting rods 121 on the first proximal support 12 may or may not be equal to the total number of second supporting rods 131 on the first distal support 13. In the present embodiment, the total number of the first supporting rods 121 may be between 3-15, the total number of the second supporting rods 131 may be between 3-15, and in another embodiment, the total number of the second supporting rods 131 and the total number of the first supporting rods 121 are equal, and may be between 6-8.

The length of the first supporting rod 121 may be between 2-8 mm, the length of the second supporting rod 131 may be between 2-10 mm, and for example, the length of the first supporting rod 121 and the length of the second supporting rod 131 may both be between 3-5 mm. As used herein, the term "length" refers to the shortest distance from the first connecting end 121a to the first free end 121b when the first supporting rod 121 is a special-shaped rod or the shortest distance from the second connecting end 131a to the second free end 131b when the second supporting rod 131 is a special-shaped rod.

With continued reference to FIG. 7, in the expanded or natural configuration, a minimum included angle a (the minimum included angle between the first distal support 13 and the central axis L when in the expanded configuration) between the second supporting rod 131 on the first distal support 13 and the central axis L of the first inner stent tube 11 ranges from 5° to 30°, for example, the minimum included angle a is 10°; and a minimum angle b (the minimum angle between the first supporting rod 121 and the first inner stent tube 11 when in the expanded configuration) between the first supporting rod 121 on the first proximal support 12 and the central axis L of the first inner stent tube 11 ranges from 20° to 80°, for example, the minimum angle b is 75°. The setting of angles is such that the first distal support 13 better fits with the first proximal support 12 to be clamped against the wall of the main stent tube C near the fenestration site, thereby preventing the first vascular stent 10 from shifting or becoming dislodged, and reducing the probability that the main stent tube C shifts.

In the expanded configuration of the first vascular stent 10, the first free end 121b of the first proximal support 12 is closer to the distal end of the first vascular stent 10 than the second free end 131b of the first distal support 13 so that the first proximal support 12 and the first distal support 13 can be better clamped against the wall of the main stent tube C.

The first proximal support 12 on the first vascular stent 10 can abut against the inner wall side of the main stent tube C near the fenestration site by an outward opening motion (equivalent to turning over), and through the first proximal support film covering 112, the gap existing between the first vascular stent 10 and the main stent tube C can be reduced, so as to avoid internal leakage of blood. Further, as shown in FIG. 7, by setting the preset included angle b between the first proximal support 12 and the central axis L of the first inner stent tube 11 to be less than 80°, the first proximal support 12 can better abut against the inner wall of the main stent tube C. Further, by appropriately reducing the preset included angle b and increasing the rod diameter of the first supporting rod 121, the supporting force between the first proximal support 12 and the main stent tube C can be effectively increased, and specifically, the smaller the preset included angle b, the larger the amount of deformation of the first proximal support 12 when the first proximal support 12 abuts the main stent tube C and the greater the force of the first proximal support 12 against the main stent tube C in the direction towards the branch vessel B; meanwhile, the greater the rod diameter of the first supporting rod 121, the greater the elastic force of the first proximal support 121, and the greater the force of the first proximal support 12 against the main stent tube C after it is attached to the main stent tube C.

With continued reference to FIG. 6, further, when the first proximal support 12 abuts against the inner wall of the main stent tube C, the reaction force of the main stent tube C against the first proximal support 12 risks shifting of the first vascular stent 10 towards the aortic tube A; so in order to avoid the risk, after the first vascular stent 10 of this embodiment is released in the branch vessel B, the second free ends 131b of the plurality of second supporting rods 131 on the first vascular stent 10 expand in a direction away from the outer wall of the first inner stent tube 11 and are supported at the outer wall side of the main stent tube C near the fenestration site, thereby achieving the purpose of anchoring the first vascular stent 10 to the main stent tube C, and reducing the probability that the first vascular stent 10 shifts towards the aortic tube A.

With continued reference to FIG. 7, in particular, in order for the first distal support 13 to effectively fit with the main stent tube C, the shortest distance between the second free end 131b of the first distal support 13 and the first connecting end 121a of the first proximal support 12 in the direction of the central axis L should be greater than 0, and in the natural configuration, the first free end 121a of the first proximal support 12 is closer to the distal end of the first vascular stent 10 than the second free end 131b of the first distal support 13. It will be understood by those skilled in the art that the second supporting rod 131 is not limited to a straight rod, for example, the second supporting rod 131 may be a special-shaped rod body. Further, the surface of the first distal support 13 may be covered with a film material as well, so that the first distal support 13 has a sealing effect on the basis of having an anchoring function to further prevent internal leakage.

Embodiment 2

Figure 8:
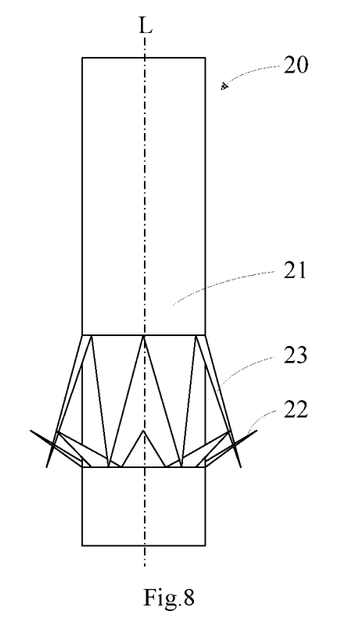
FIG. 8 is a structural schematic view of a second vascular stent according to a second embodiment of the disclosure.

The same parts of the second vascular stent 20 of Embodiment 2 as those of the first vascular stent 10 of Embodiment 1 will not be described in detail here, and the main difference between them is that, as shown in FIG. 8, this Embodiment 2 provides a second stent 20 consisting of a second inner stent tube 21, a second proximal support 22 and a second distal support 23, where the second proximal support 22 and the second distal support 23 are each composed of a plurality of V-shaped connecting rods, which may be formed by knitting nickel-titanium wires, or by cutting and heat-setting nickel-titanium tubes, and which may be connected to one another or may be provided on the second inner stent tube 21 at intervals. At least a layer of film is provided on each of the plurality of V-shaped connecting rods of the second proximal support 22 and the plurality of V-shaped connecting rods of the second distal support 23 to prevent internal leakage. The connecting ends of the plurality of V-shaped connecting rods can be connected to the second inner stent tube 21 through winding, welding and the like, the free ends of the plurality of V-shaped connecting rods are far away from the second inner stent tube 21 when the plurality of V-shaped connecting rods expand in a self-expansion manner, and specifically, the free ends of the plurality of V-shaped connecting rods are far away from the second inner stent tube 21 in a natural configuration or in an expanded configuration. The plurality of V-shaped connecting rods of the second proximal support 22 are circumferentially distributed on the outer wall of the second inner stent tube 21, and form an included angle of 70° with the central axis L of the second inner stent tube 21, and the plurality of V-shaped connecting rods of the second distal support 23 are circumferentially distributed on the outer wall of the second inner stent tube 21 and form an included angle of 10° with the central axis L of the second inner stent tube 21.

In another embodiment, the plurality of V-shaped connecting rods of the second distal support 23 may be a metal framework without a film material, and the metal framework may be formed by connecting 3 to 10 V-shaped connecting rods along the outer wall of the second inner stent tube 21, for example, the metal framework may be formed by 5 V-shaped connecting rods. The plurality of V-shaped connecting rods of the second proximal support 22 and the plurality of V-shaped connecting rods of the second distal support 23 may be distributed in one-to-one correspondence along the circumferential direction of the second inner stent tube 21, and may be staggered along the circumferential direction of the second inner stent tube 21, and meanwhile, the number of V-shaped connecting rods in the second proximal support 22 and the number of V-shaped connecting rods in the second distal support 23 may be equal or unequal. Further, the plurality of V-shaped connecting rods of the second proximal support 22 and the plurality of V-shaped connecting rods of the second distal support 23 may be the same or different in size, and when each of the plurality of V-shaped connecting rods is different in size, the plurality of V-shaped connecting rods are capable of anchoring the second vascular stent 10 to the main stent tube when the second vascular stent 10 is tilted relative to the main stent tube.

The V-shaped connecting rod of this Embodiment 2 has a larger supporting surface and supporting force than a single supporting rod, and therefore, the second proximal support 22 and the second distal support 23 of this Embodiment 2 can provide better stability after the second vascular stent 20 is implanted into a target area in the body. Each of the V-shaped connecting rods in this Embodiment 2 has one free end and two connecting ends, so that the plurality of V-shaped connecting rods connected with one another can ensure that the anchoring effect of the second proximal supporter 22 and the second distal supporter 23 is not affected by the local deformation of the V-shaped connecting rods when the respective free ends are unilaterally stressed in a bent blood vessel or under compression.

In another embodiment, the second proximal support 22 and the second distal support 23 may each be composed of a plurality of corrugated connecting rods, which differ from V-shaped connecting rods in that the corrugated connecting rods are rods with corrugated shape. The implementations of the corrugated connecting rod are similar to those of the V-shaped connecting rod, and therefore, a detailed description thereof will be omitted.

Embodiment 3

Figure 9:
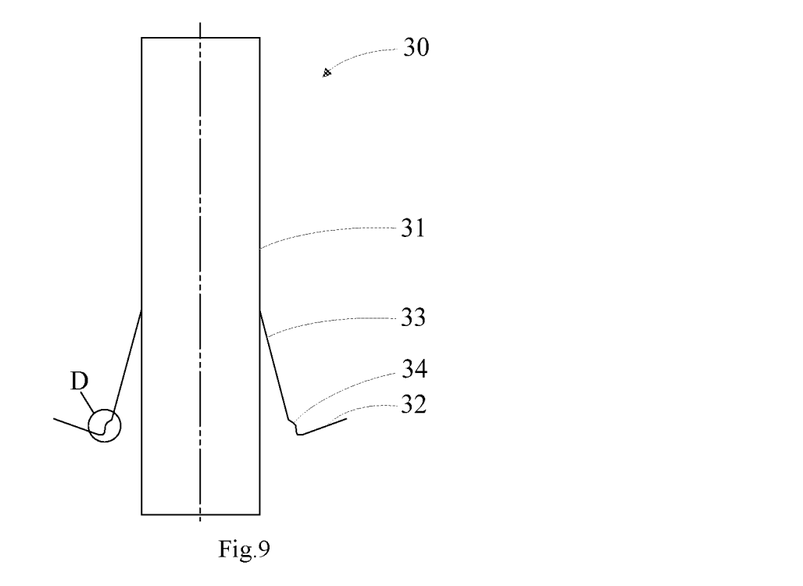
FIG. 9 is a structural schematic view of a third vascular stent according to a third embodiment of the disclosure.
Figure 10:
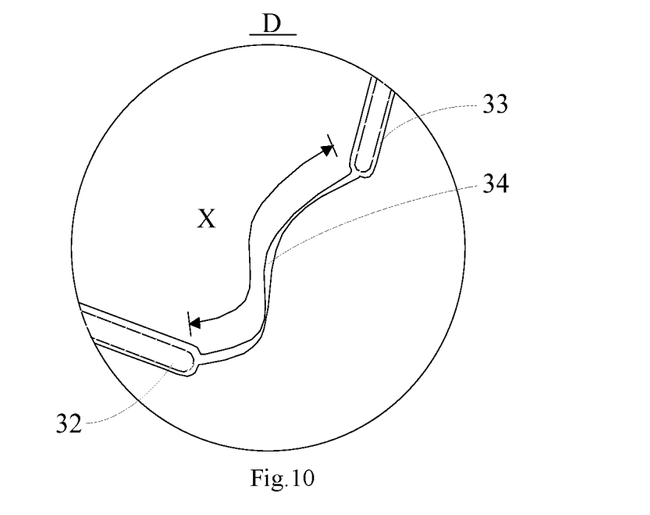
FIG. 10 is a structural schematic view of a portion D of the third vascular stent shown in FIG. 9.

The same parts of the third vascular stent 30 of Embodiment 3 as those of the first vascular stent 10 of Embodiment 1 will not be described in detail here, and the main difference between them is that, as shown in FIGS. 9 and 10, Embodiment 3 provides a third stent 30 consisting of a third inner stent tube 31, a third proximal support 32 and a third distal support 33, where the third proximal support 32 is provided with at least a layer of film to prevent internal leakage. The third proximal support 32 and the third distal support 33 may be composed of a plurality of single supporting rod frames; the connecting end of the third proximal support 32 is connected to the free end of the third distal support 33 by a flexible connector 34, which may be formed of a film material, for example, the flexible connector 34 integrally covers the metal framework of the third proximal support 32; and the metal framework of the third distal support 33 spaced apart from the third proximal support 32, and the third proximal support 32 and the third distal support 33 are welded to form a unitary supporting structure. The metal framework of the third proximal support 32 is not in direct contact with the metal framework of the third distal support 33; and a maximum distance X between them, i.e. the length of the flexible connection 34 is greater than 0 mm and less than or equal to 2 mm, for example the length of the flexible connection 34 is 2 mm. If the flexible connector 34 is not provided, the connecting end of the third proximal support 32 is directly connected to the free end of the third distal support 33, and then the third distal support 33 cannot expand after being released, and the third proximal support 32 cannot serve as an anchor. If the length of the flexible connector 34 is greater than 2 mm, the anchoring effect of the third proximal support 32 may be affected, or even the third proximal support 32 cannot serve as an anchor because the flexible connector 34 is too long.

Figure 11:
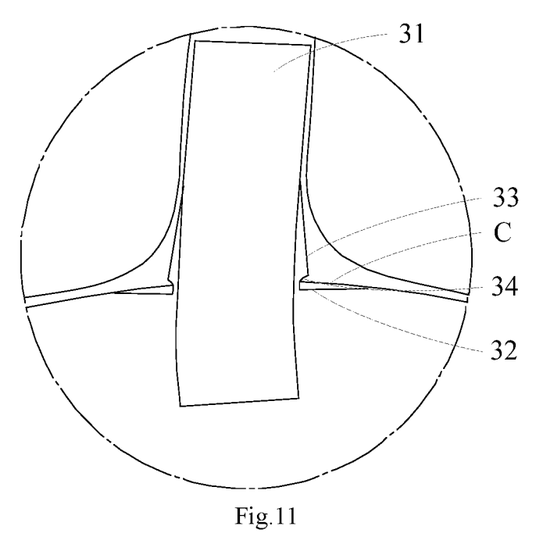
FIG. 11 is a structural schematic view showing the third vascular stent shown in FIG. 9 being implanted into the main stent tube.

As shown in FIG. 11, a portion of the third vascular stent 30 is implanted into the branch vessel through the fenestration on the main stent tube C. After releasing the third vascular stent 30, the third proximal support 32 abuts the inner wall of the main stent tube C near the fenestration site by expanding towards the distal end of the third vascular stent 30, and the flexible connector 34 is located at the fenestra edge of the main stent tube C; then, the third distal support 33 abuts against the outer wall of the main stent tube C near the fenestration site by expanding outwardly in a direction away from the outer wall of the third inner stent tube 31. Since the end of the third distal support 33 connected to the flexible connector 34 abuts against the outer wall of the main stent tube C, the free end of the third proximal support 32 abuts against the inner wall of the main stent tube C, thereby anchoring the third vascular stent 30 to the main stent tube C, preventing the third vascular stent 30 from shifting or becoming dislodged, and meanwhile avoiding internal leakage. It should be noted that since there is no rigid connection between the third distal support 33 and the third proximal support 32, and the flexible connector 34 has a certain deformability, the flexible connector 34 causes less resistance to the third proximal support 32 and the third distal support 33 during expansion of the third proximal support 32 and the third distal support 33, thereby facilitating smooth expansion of the third proximal support 32 and the third distal support 33.

The connecting end of the third proximal support 32 is connected to the free end of the third distal support 33, so that the third proximal support 32 in this Embodiment 3 can be expanded more fully, covering a larger area, thereby enhancing the anchoring stability of the third vascular stent 30. At the same time, the flexible connector 34 between the connecting end of the third proximal support 32 and the free end of the third distal support 33 also improves the sealability of the third stent 30 to prevent internal leakage.

The third distal support 33 may be composed of a plurality of single supporting rods, the third distal support 33 serves as a unilateral anchor for the third vascular stent 30, and the implementation of the third distal support 33 is the same as that of the first distal support 13 in Embodiment 1 and will not be described in detail herein.

The third proximal support 32 and the third distal support 33 may be connected by the flexible connector 34 formed of a polymer wire such as PTFE, polyester, and polypropylene. The lengths of the plurality of connecting rods in the third distal support 33 may be the same or different, and the connecting rods may be circumferentially spaced or continuously uniformly or non-uniformly distributed along the outer wall of the third inner stent tube 31, so that the third distal support 33 and the third proximal support 32 can maintain anchoring stability when the third stent 30 is in a complex environment.

Figure 12:
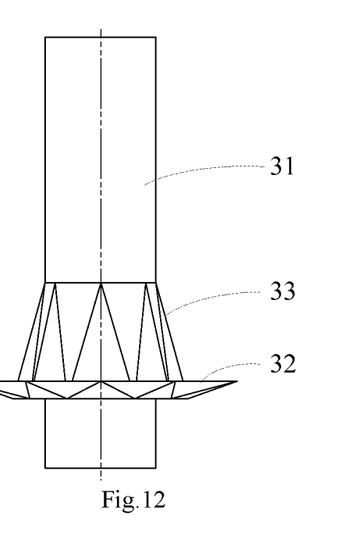
FIG. 12 is a structural schematic view of the third vascular stent according to another embodiment of the disclosure.

As shown in FIG. 12, in another embodiment, the third proximal support 32 and the third distal support 33 may each be composed of a plurality of V-shaped connecting rods, the connecting ends of the V-shaped connecting rods of the third proximal support 32 and the free ends of the V-shaped connecting rods of the third distal support 33 are connected by a flexible connector, and the V-shaped connecting rods have better anchoring stability relative to the single supporting rods. The implementation in which the third proximal support 32 and the third distal support 33 are provided as V-shaped connecting rods is similar to the implementation in which the third proximal support 32 and the third distal support 33 are provided as single supporting rods, and will not be described in detail herein. Further, at least one coating layer of film may be provided on the third distal support 33 to improve the sealability of the third stent 30 to further prevent internal leakage.

It should be noted that each structure on each vascular stent described in Embodiment 1, Embodiment 2 and Embodiment 3 can be reasonably combined according to the actual application environment, and the combined vascular stent can include one or more of the above-mentioned technical features and has the technical effects of each technical feature, so that the combined vascular stent falls within the protection scope of the vascular stent of the disclosure.

The above description is only preferred implementations of the disclosure and the protection scope of the disclosure is not limited thereto. Any modifications and substitutions that those skilled in the art can easily think of fall within the technical scope disclosed by the disclosure Accordingly, the protection scope of the disclosure shall be subject to the protection scope defined by the claims.

The invention claimed is:

1. A vascular stent, comprising: an inner stent tube as well as a proximal support and a distal support which are disposed on an outer wall of the inner stent tube, when the vascular stent is in a compressed configuration, the proximal support and the distal support are both folded towards the outer wall of the inner stent tube; and when the vascular stent is expanded from the compressed configuration to an expanded configuration, a free end of the proximal support extends towards a distal end of the vascular stent, and a free end of the distal support extends towards a proximal end of the vascular stent, the free end of the proximal support is closer to the distal end of the vascular stent than the free end of the distal support.

2. The vascular stent according to claim 1, wherein the proximal support comprises a plurality of first supports disposed along a circumferential direction of the inner stent tube, connecting ends of the plurality of first supports are each connected to the outer wall of the inner stent tube, and free ends of the plurality of first supports are each directed towards an outside of the inner stent tube.

3. The vascular stent according to claim 2, wherein a minimum included angle between a straight line or plane in which the first support is located and a central axis of the vascular stent ranges from 20° to 80° in the expanded configuration or a natural configuration.

4. The vascular stent according to claim 2, wherein the proximal support is provided with at least a layer of film.

5. The vascular stent according to claim 1, wherein the distal support comprises a plurality of second supports disposed along a circumferential direction of the inner stent tube, connecting ends of the plurality of second supports are each connected to the outer wall of the inner stent tube, and free ends of the plurality of second supports are each directed towards a proximal end of the inner stent tube.

6. The vascular stent according to claim 5, wherein a minimum included angle between a straight line or plane in which the second support is located and the central axis of the vascular stent ranges from 5° to 30° in the expanded configuration or the natural configuration.

7. The vascular stent according to claim 1, wherein the free end of the distal support is connected to the connecting end of the proximal support by means of a flexible connector, and the free end of the proximal support expands towards the distal end of the vascular stent during expansion.

8. The vascular stent according to claim 7, wherein the flexible connector is a film, both ends of which cover the proximal support and the distal support, respectively.

9. The vascular stent according to claim 8, wherein a length of the flexible connector is greater than 0 mm and less than or equal to 2 mm.

\* \* \* \* \*